United States Patent
Utsui et al.

[19]

[11] Patent Number: 5,891,016
[45] Date of Patent: Apr. 6, 1999

[54] FLUORESCENCE ENDOSCOPE HAVING AN EXCITING LIGHT FILTER AND A FLUORESCENCE FILTER

[75] Inventors: Tetsuya Utsui; Rensuke Adachi; Hirohisa Ueda; Hiroshi Sano, all of Tokyo, Japan

[73] Assignee: Asahi Kogaku Kogyo Kabushiki Kaisha, Tokyo, Japan

[21] Appl. No.: 741,467

[22] Filed: Oct. 30, 1996

[30] Foreign Application Priority Data

Nov. 9, 1995 [JP] Japan ................................ 7-290854

[51] Int. Cl.⁶ ........................................ A61B 1/06
[52] U.S. Cl. ........................ 600/181; 600/160; 600/476
[58] Field of Search ........................... 600/109, 181, 600/407, 310, 312, 342, 476, 478

[56] References Cited

U.S. PATENT DOCUMENTS

| | | | |
|---|---|---|---|
| 4,821,117 | 4/1989 | Sekiguchi | 60/178 X |
| 5,102,625 | 4/1992 | Milo | 422/82.07 |
| 5,507,287 | 4/1996 | Palcic et al. | |

FOREIGN PATENT DOCUMENTS 4133493   4/1992   Germany ................................ 600/181

OTHER PUBLICATIONS

Japanese Unexamined Patent Publication No. 4-150845.

*Primary Examiner*—John P. Leubecker
*Attorney, Agent, or Firm*—Kane,Dalsimer,Sullivan, Kurucz, Levy,Eisele and Richard, LLP

[57] ABSTRACT

An exciting light filter through which exciting light which is adapted to radiate fluorescence from a living tissue is transmitted, is provided in an illumination light path defined between a light source which emits the illumination light and an object to be observed, in a fluorescence endoscope. A fluorescence filter which permits fluorescence which is radiated from the living tissue due to the illumination by the exciting light and whose wavelength is longer than that of the exciting light to pass therethrough but does not permit the exciting light to pass through the fluorescence filter, is provided in an observation light path defined between the object and a viewing portion in which an image of the object is viewed. There is a difference of 20 nm to 40 nm between the longest wavelength of the wavelength band of which more than 10% are transmitted through the exciting light filter and the shortest wavelength of the wavelength band of which more than 10% are transmitted through the fluorescence filter.

11 Claims, 2 Drawing Sheets

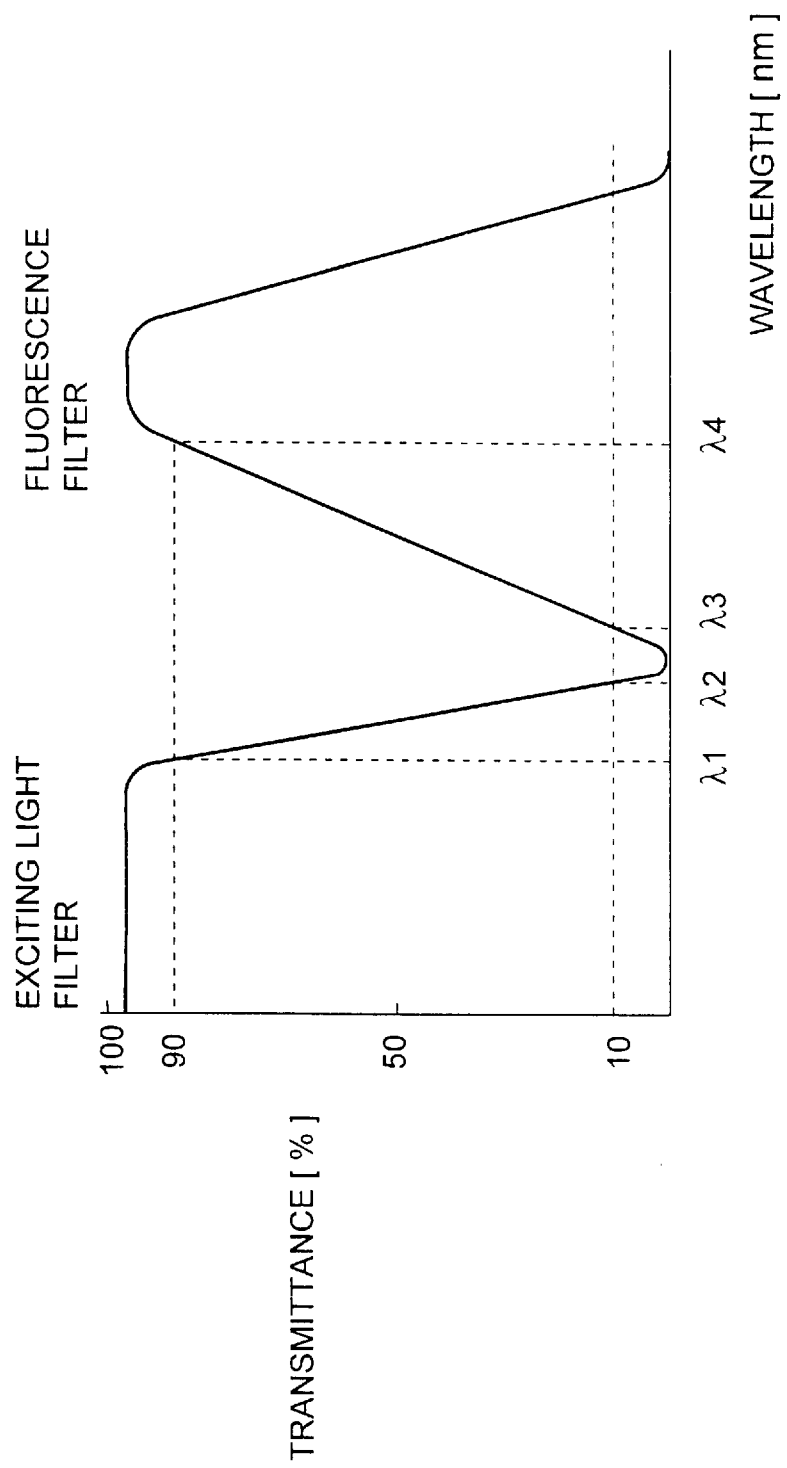
F I G. 1

FLUORESCENCE ENDOSCOPE HAVING AN EXCITING LIGHT FILTER AND A FLUORESCENCE FILTER

BACKGROUND OF THE INVENTION

1. Field of the Invention

The present invention relates to a fluorescence endoscope which is used for directly visually observing a living tissue, using fluorescence which is radiated from the living tissue when visual light is impinged upon the living tissue.

2. Description of the Related Art

In general, in a fluorescence endoscope, an exciting light filter is provided in an illumination light path defined between a light source (lamp) and an object to be examined. Exciting light, adapted to radiate fluorescence from the living tissue, can be transmitted through the endoscope. A fluorescence observing filter (fluorescence filter) is provided in the illumination light path. The fluorescence observing filter permits fluorescence radiated from the living tissue, in response to the exciting light and having a wavelength longer than that of the exciting light, to pass therethrough and does not permit the exciting light to pass through the fluorescence filter.

The wavelength band of the exciting light which excites the living tissue to radiate fluorescence therefrom is approximately 420 nm to 480 nm and the optimal wave length band for the radiation of fluorescence is approximately 450 nm to 475 nm.

On the other hand, the wavelength band of the fluorescence radiated from the living tissue is approximately 480 nm to 600 nm and the peak value of the intensity thereof is obtained at 480 nm to 520 nm, adjacent to the wavelength band of the exciting light.

Since the intensity of the fluorescence produced by the exciting light is extremely small in comparison with the exciting light, even a small amount of exciting light which reaches the observing portion makes it difficult to observe the fluorescence. To this end, the exciting light filter and the fluorescence filter must be produced so that the wavelength band which can pass through the exciting light filter and the wavelength band which can pass through the fluorescence filter do not overlap.

However, since the wavelength bands of the exciting light and the fluorescence are adjacent as mentioned above and they exhibit the peak values of the intensity within limited ranges, if the exciting light transmission range of the exciting light filter is located away from the fluorescence transmission range of the fluorescence filter, the amount of light transmitted through the filter is reduced, so that the intensity of the fluorescence to be observed is weakened, thus resulting in a diagnosis error.

In theory, it is ideal that the exciting light filter and the fluorescence filter are prepared so that the longest wavelength of the light transmitted through the exciting light filter is identical or almost identical to the shortest wavelength of the light transmitted through the fluorescence filter.

The longest wavelength or the shortest wavelength transmitted through the filter refers to the wavelength at which the transmittance of the filter is zero, and hence it is extremely difficult to optically measure the longest wavelength or shortest wavelength. This is the reason that it is very difficult to produce the filter with reference to the longest wavelength that can pass through the exciting light filter or the shortest wavelength that can pass through the fluorescence filter.

SUMMARY OF THE INVENTION

It is an object of the present invention to provide a fluorescence endoscope in which, using an exciting light filter and a fluorescence filter, good visual observation using fluorescence can be easily obtained.

To achieve the object of the present invention, there is provided a fluorescence endoscope in which an exciting light filter, through which exciting light which is adapted to radiate fluorescence from a living tissue is transmitted is provided in an illumination light path defined between a light source lamp which emits the illumination light and an object to be observed, and a fluorescence filter which permits fluorescence which is radiated from the living tissue due to the illumination by the exciting light and whose wavelength is longer than that of the exciting light to pass therethrough but does not permit the exciting light to pass through the fluorescence filter is provided in an observation light path defined between the object and a viewing portion in which an image of the object is viewed. There is a difference of 20 nm to 40 nm between the longest wavelength of the wavelength band of which more than 10% are transmitted through the exciting light filter and the shortest wavelength of the wavelength band of which more than 10% are transmitted through the fluorescence filter.

Preferably, the longest wavelength of the wavelength band of which more than 10% pass through the exciting light filter is 455 nm to 460 nm, and the shortest wavelength of the wavelength band of which more than 10% pass through the fluorescence filter is 480 nm to 495 nm.

In the preferred embodiment, in the transmission wavelength band of the exciting light filter on the long wavelength side, the wavelength band in which the transmission changes from 90% to 10% is 12 nm to 20 nm.

Also, in the transmission wavelength band of the fluorescence filter on the short wavelength side, it is preferable that the wavelength band in which the transmission changes from 10% to 90% be 13 nm to 30 nm.

The present disclosure relates to subject matter contained in Japanese Patent Application No. 07-290854 (filed on Nov. 9, 1995) which is expressly incorporated herein by reference in its entirety.

BRIEF DESCRIPTION OF THE DRAWINGS

The invention will be described below in detail with reference to the accompanying drawings, in which:

FIG. 1 is a graph showing spectral transmission characteristics of a fluorescence endoscope according to the present invention; and, FIG. 2 is a conceptual view of a fluorescence endoscope according to the present invention.

DESCRIPTION OF THE PREFERRED EMBODIMENTS

Figure 2:
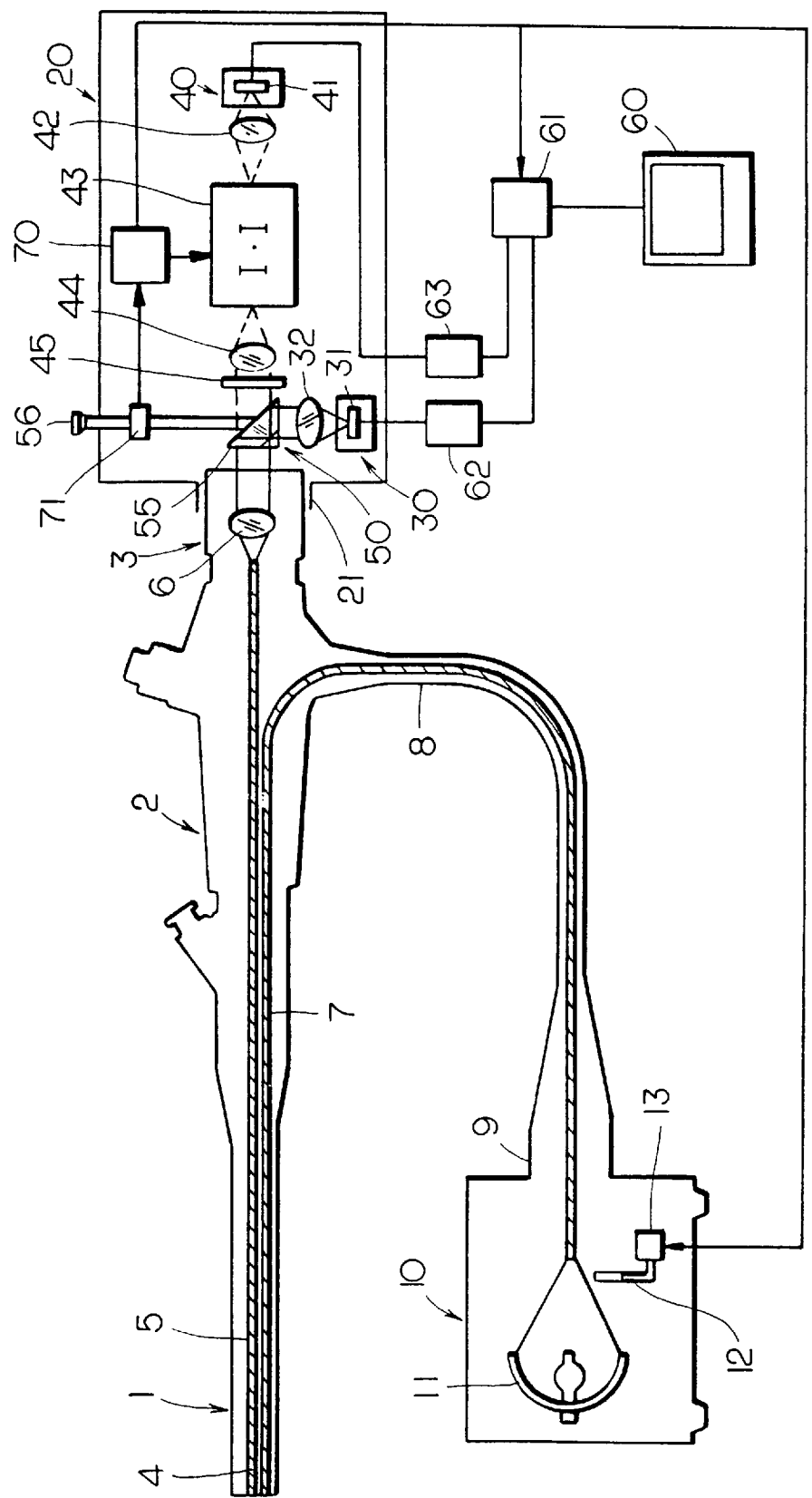

FIG. 2 shows a whole structure of a fluorescence endoscope in which 1 designates the insertion portion of the endoscope and 2 designates the operation portion connected to the base end of the insertion portion 1. The insertion portion 1 is provided with an (optical) objective system 4 incorporated in the front end thereof to form an image of an object onto the incident end surface of a bundle of image guiding fibers (an image guide fiber bundle) 5. The image guide fiber bundle 5 extends through the operation portion 2 from the insertion portion 1 and reaches an eyepiece portion 3, at the emission end thereof. The eyepiece portion 3 is provided with an ocular system 6 incorporated therein to provide an enlarged view of the emission end of the image guide fiber bundle 5.

An image of an object located in front of the insertion portion 1 is formed on the incident end surface of the image guide fiber bundle 5 by the objective system 4. The image thus formed is transmitted to the eyepiece portion 3 through the image guide fiber bundle 5. Thus, the object image can be directly and visually observed through the ocular system 6 when the eyepiece portion 3 is not connected to a TV camera unit 20 commonly used for regular light and fluorescence.

A bundle of light guiding fiber (light guide fiber bundle) 7 through which illumination light with which the object is illuminated is transmitted extends in the objective system 4 and the insertion portion 1 and reaches, at the incident end thereof, a detachable connector 9 which is detachably attached to a light source apparatus 10 through a light guide connecting tube 8.

A lamp 11 in the form of a xenon lamp is provided in the light source 10, so that the illumination light emitted from the lamp 11 is converged and made incident upon the light guide fiber bundle 7 at the incident end thereof and is emitted from the emission end of the light guide fiber bundle 7 toward the object to illuminate the same.

An exciting light filter 12 which permits more than 10% of wavelength of for example 380 nm to 460 nm to pass therethrough (i.e., transmittance of more than 10%) is retractably inserted in the illumination light path between the incident end surface of the light guide fiber bundle 7 and the lamp 11 by means of a solenoid 13.

The exciting light filter 12 is retracted from the illumination light path upon normal observation, as shown in FIG. 2 and is inserted in the illumination light path upon an observation using fluorescence (fluorescence observation). The inserted position of the exciting light filter 12 is not shown.

The eyepiece portion 3 can be detachably connected to the regular/fluorescence TV camera unit 20. The latter is provided with a normal image pickup TV camera 30 incorporated therein, which is adapted to pickup the regular (normal) object image transmitted through the ocular system 6 and a fluorescence image pickup TV camera 40 incorporated in the TV camera 20, which is adapted to pickup the fluorescence image transmitted through the ocular system 6. The TV cameras 30 and 40 are integrally formed as a single unit.

The normal image pickup TV camera 30 has a solid-state image pickup device 31 and an imaging lens 32. The fluorescence image pickup TV camera 40 has a solid-state image pickup device 41 and an imaging lens 42. Consequently, when the eyepiece portion 3 of the endoscope is attached to or detached from the regular/fluorescence TV camera unit 20, the endoscope is attached to or detached from the normal image pickup TV camera 30 and the fluorescence image pickup TV camera 40 together.

The fluorescence image pickup TV camera 40 is provided with an image intensifier (I.I.) 43 which remarkably amplifies the intensity of the light transmitted through the ocular system 6. 44 designates the imaging lens to form the object image transmitted through the ocular system 6 onto the incident end surface of the image intensifier 43.

A fluorescence filter 45 which permits more than 10% of wavelength of for example 480 nm to 580 nm to pass therethrough (i.e., transmittance of more than 10%) is provided in front of the imaging lens 44, so that only the light whose wavelength can pass through the fluorescence filter 45 can be made incident upon the image intensifier 43. The light whose wavelength passes through the exciting light filter 12 does not pass through the fluorescence filter 45.

When the light whose wavelength passes through the exciting light filter 12 is emitted toward the living tissue, the normal tissue radiates fluorescence of wavelength which passes through the fluorescence filter 45 but no fluorescence is radiated from, for example, cancer tissue or the like. Consequently, when the exciting light filter 12 is inserted in the illumination light path, the fluorescence radiated from the normal tissue only of the object (living tissue) is made incident upon and intensified by the image intensifier 43.

A light path switching optical system 50 is provided in the front end of the regular/fluorescence TV camera unit 20 to switch the light path of the light transmitted through the ocular system 6 between a first light path connecting with the TV camera 30 and a second light path connecting with the TV camera 40.

The light path switching optical system 50 is comprised of a roof prism 55 which is provided with a reflecting surface inclined at 45° with respect to the optical axis of the ocular system 6 and which is movable in a direction perpendicular to the optical axis of the ocular system 6. The movement of the roof prism 55 is carried out by an operation rod 56.

Consequently, when the roof prism 55 is located on the optical axis of the ocular system 6 as shown in FIG. 2, the image transmitted through the ocular system 6 is reflected laterally by the roof prism 55 and is formed on the solid-state image pickup device 31 of the normal image pickup TV camera 30.

When the roof prism 55 is laterally moved and retracted from the optical axis of the ocular system 6, the image transmitted through the ocular system 6 passes through the fluorescence filter 45 and is formed on the light receiving surface of the image intensifier 43, as indicated by a phantom line in FIG. 2. The light intensity of the image is intensified by the image intensifier 43. Consequently, the image is formed on the solid-state image pickup device 41 of the fluorescence image pickup TV camera 40.

In the illustrated embodiment, there is a single TV monitor 60 to which the image signal output from the regular image pickup TV camera 30 or the fluorescence image pickup TV camera 40 is sent. The selection of the image signals from the TV cameras 30 and 40 is effected by a line selector 61. Numerals 62 and 63 represent controllers for the TV cameras 30 and 40, respectively.

A controller 70 having a micro processor incorporated therein outputs control signals to control the operation of the image intensifier 43, the line selector 61 and the exciting light filter 12, etc., in association with the switching operation of the light path switching optical system 50. A detector 71 detects the switching state of the light path switching optical system 50 and supplies the detection signal to the controller 70.

Consequently, upon normal observation, the exciting light filter 12 is retracted from the illumination light path in the light source apparatus 10, as shown in FIG. 2, so that the object is illuminated by the normal illumination light. Thus, the observed object image is picked-up by the regular image pickup TV camera 30.

On the regular/fluorescence TV camera unit 20 side, the power source of the image intensifier 43 is turned OFF, and the line selector 61 is switched to the normal image pickup TV camera 30. Consequently, the observed normal image formed by the whole wavelength of the visible light is indicated in the TV monitor 60 in accordance with the image signal output from the solid-state image pickup device 31 of the normal image pickup TV camera 30.

When the light path switching optical system 50 is switched to move the roof prism 55 in the lateral direction so that the roof prism 55 is retracted from the illumination light path, while keeping the eyepiece portion 3 connected to the regular/fluorescence TV camera 20, the exciting light filter 12 is inserted in the illumination light path and the power source of the image intensifier 43 is turned ON. Consequently, the line selector 61 is switched to the fluorescence image pickup TV camera 40.

As a result, the object is illuminated by the illumination light (exciting light) whose wavelength passes through the exciting light filter 12. The observed image is transmitted through the fluorescence filter 45 and is made incident upon the image intensifier 43.

Thus, only the light whose wavelength passes through the fluorescence filter 45 is made incident upon the image intensifier 43. Namely, the fluorescence radiated from the object is only made incident upon the image intensifier 43, so that the intensified fluorescence image is picked-up by the solid-state image pickup device 41 of the fluorescence image pickup TV camera 40 and is indicated in the TV monitor 60.

<EXAMPLE 1>

FIG. 1 shows spectral transmission characteristics of the exciting light filter 12 and the fluorescence filter 45. In the downward curved portion of the transmission wavelength band of the exciting light filter 12 on the long wavelength side in FIG. 1, the wavelength at which the transmission is 90% is $\lambda 1$ and the wavelength at which the transmission is 10% is $\lambda 2$, respectively. Also, in the raised portion of the transmission wavelength band of the fluorescence light filter 45 on the short wavelength side in FIG. 1, the wavelength at which the transmission is 10% is $\lambda 3$ and the wavelength at which the transmission is 90% is $\lambda 4$, respectively.

In general, for a filter, it is practically extremely difficult to measure the wavelength at which the transmission is 0% or 100%, but the wavelength at which the transmission is 10% or 90% can be easily optically measured.

In Example 1 in which the exciting light filter 12 and the fluorescence filter 45 having the following optical characteristics were used, a light and clear fluorescence observation could be carried out.

$\lambda 1$: 435 nm
$\lambda 2$: 455 nm
$\lambda 3$: 495 nm
$\lambda 4$: 525 nm

<EXAMPLE 2>

In Example 2, the exciting light filter 12 and the fluorescence filter 45 having the following optical characteristics were used. Similarly to Example 1, a light and clear fluorescence observation could be carried out.

$\lambda 1$: 440 nm
$\lambda 2$: 458 nm
$\lambda 3$: 488 nm
$\lambda 4$: 513 nm

<EXAMPLE 3>

In Example 3, the exciting light filter 12 and the fluorescence filter 45 having the following optical characteristics were used. Similarly to Example 1, a light and clear fluorescence observation could be carried out.

$\lambda 1$: 448 nm
$\lambda 2$: 460 nm
$\lambda 3$: 480 nm
$\lambda 4$: 493 nm

As can be understood from the above discussion, according to the present invention, since the exciting light filter and the fluorescence filter are formed such that there is a predetermined difference between the longest wavelength of the wavelength band of which more than 10% pass through the exciting light filter and the shortest wavelength of the wavelength band of which more than 10% pass through the fluorescence filter, the transmission wavelength bands do not overlap. Moreover, according to the present invention, the exciting light filter and the fluorescence filter whose transmission wavelength band is located adjacent or very closely to the transmission wavelength band of the exciting light filter can be easily prepared, based on the precise measurement of the wavelength.

What is claimed is:

1. A fluorescence endoscope in which living tissue is illuminated by exciting light and radiated fluorescence light from said living tissue is received and said radiated fluorescence wavelength is longer than that of said exciting light, said fluorescence endoscope comprising:

a light source lamp, which emits illumination light;

an illumination light path defined between said light source lamp and an object to be observed;

a viewing portion in which an image of said object is viewed;

an observation light path defined between said object and said viewing portion;

an exciting light filter through which exciting light which is adapted to radiate fluorescence from a living tissue is transmitted, said exciting light filter being provided in said illumination light path; and a fluorescence filter, which permits fluorescence which is radiated from said living tissue due to illumination by said exciting light to pass therethrough but does not permit said exciting light to pass therethrough, said fluorescence filter being provided in said observation light path;

wherein there is a difference of 20 nm to 40 nm between said longest wavelength of said wavelength band of which more than 10% are transmitted through said exciting light filter and said shortest wavelength of said wavelength band of which more than 10% are transmitted through said fluorescence filter.

2. The fluorescence endoscope according to claim 1, wherein said longest wavelength of said wavelength band more than 10% of which pass through said exciting light filter is 455 nm to 460 nm.

3. The fluorescence endoscope according to claim 2, wherein said shortest wavelength of said wavelength band of which more than 10% pass through said fluorescence filter is 480 nm to 495 nm.

4. The fluorescence endoscope according to claim 1, wherein said transmission wavelength band of said exciting light filter on said long wavelength side, in which said transmission changes from 90% to 10% is 12 nm to 20 nm.

5. The fluorescence endoscope according to claim 4, wherein in said transmission wavelength band of said fluorescence filter on said short wavelength side, in which said transmission changes from 10% to 90% is 13 nm to 30 nm.

6. The fluorescence endoscope according to claim 1, wherein on said long wavelength side of said exciting light filter, at which said transmission is 90% said transmission wavelength $\lambda 1$ is 435 nm, and at which said transmission is 10% said transmission wavelength $\lambda 2$ is 455 nm.

7. The fluorescence endoscope according to claim 6, wherein on said short wavelength side of said fluorescence filter, at which said transmission is 10% said transmission wavelength $\lambda 3$ is 495 nm, and at which said transmission is 90% said transmission wavelength $\lambda 4$ is 525 nm.

8. The fluorescence endoscope according to claim 1, wherein on said long wavelength side of said exciting light filter, at which said transmission is 90% said transmission wavelength $\lambda 1$ is 440 nm, and at which said transmission is 10% said transmission wavelength $\lambda 2$ is 458 nm.

9. The fluorescence endoscope according to claim 8, wherein on said short wavelength side of said fluorescence filter, at which said transmission is 10% said transmission wavelength $\lambda 3$ is 488 nm, and at which said transmission is 90% said transmission wavelength $\lambda 4$ is 513 nm.

10. The fluorescence endoscope according to claim 1, wherein on said long wavelength side of said exciting light filter, at which said transmission is 90% said transmission wavelength $\lambda 1$ is 448 nm, and at which said transmission is 10% said transmission wavelength $\lambda 2$ is 460 nm.

11. The fluorescence endoscope according to claim 10, wherein on said short wavelength side of said fluorescence filter, at which said transmission is 10% said transmission wavelength $\lambda 3$ is 480 nm, and at which said transmission is 90% said transmission wavelength $\lambda 4$ is 493 nm.

* * * * *